United States Patent [19]
Otis, Jr. et al.

[11] Patent Number: 5,917,429
[45] Date of Patent: Jun. 29, 1999

[54] CONTACTLESS COMMUNICATION SYSTEM

[75] Inventors: Alton B. Otis, Jr., San Francisco; Darrell Ingram, Palo Alto; Tom Papanek, Menlo Park, all of Calif.

[73] Assignee: Aprex Corporation, Menlo Park, Calif.

[21] Appl. No.: 08/613,279

[22] Filed: Mar. 11, 1996

Related U.S. Application Data

[63] Continuation of application No. 07/953,691, Sep. 28, 1992, abandoned, which is a continuation-in-part of application No. 07/944,462, Sep. 14, 1992, abandoned.

[51] Int. Cl.⁶ .................................................. G08C 19/06
[52] U.S. Cl. ........................ 340/870.31; 340/309.15; 340/309.4; 340/568.1; 340/573; 368/10
[58] Field of Search ......................... 340/309.15, 573, 340/870.31, 309.3, 309.4, 825.19, 540, 568.1, 870.32; 221/2–15; 368/10

[56] References Cited

U.S. PATENT DOCUMENTS

| | | |
|---|---|---|
| 3,917,045 | 11/1975 | Williams et al. . |
| 3,998,356 | 12/1976 | Christensen .................................. 221/2 |
| 4,034,757 | 7/1977 | Glover . |
| 4,125,871 | 11/1978 | Martin .................................... 364/900 |
| 4,223,801 | 9/1980 | Carlson ..................................... 368/10 |
| 4,360,125 | 11/1982 | Martindale et al. ......................... 221/2 |
| 4,419,016 | 12/1983 | Zoltan ........................................ 368/10 |
| 4,447,224 | 5/1984 | DeCant, Jr. et al. . |
| 4,473,884 | 9/1984 | Behl ........................................ 364/479 |
| 4,494,950 | 1/1985 | Fischell ..................................... 604/66 |
| 4,504,153 | 3/1985 | Schollmeyer et al. ................... 364/569 |
| 4,518,267 | 5/1985 | Hepp . |
| 4,526,474 | 7/1985 | Simon ....................................... 368/10 |
| 4,561,443 | 12/1985 | Hogrefe et al. . |
| 4,588,303 | 5/1986 | Wirtschafter et al. .................... 368/10 |
| 4,604,847 | 8/1986 | Moulding, Jr. et al. . |
| 4,616,316 | 10/1986 | Hanpeter et al. ....................... 364/479 |
| 4,617,557 | 10/1986 | Gordon . |
| 4,619,653 | 10/1986 | Fischell ................................... 604/891 |
| 4,660,991 | 4/1987 | Simon ....................................... 368/10 |
| 4,662,537 | 5/1987 | Wolf . |
| 4,674,652 | 6/1987 | Aten et al. .............................. 364/479 |
| 4,682,299 | 7/1987 | McIntosh et al. ....................... 364/569 |
| 4,695,954 | 9/1987 | Rose et al. ............................ 364/413.02 |
| 4,725,997 | 2/1988 | Urquhart et al. .......................... 368/10 |
| 4,748,600 | 5/1988 | Urquhart .................................... 368/10 |
| 4,784,645 | 11/1988 | Fischell ................................... 604/153 |
| 4,823,982 | 4/1989 | Aten et al. .................................. 221/3 |
| 4,831,562 | 5/1989 | McIntosh et al. ....................... 364/569 |
| 4,837,719 | 6/1989 | McIntosh et al. ..................... 364/413.01 |
| 4,839,806 | 6/1989 | Goldfischer et al. ............... 364/413.02 |
| 4,849,948 | 7/1989 | Davis et al. ............................... 368/10 |
| 4,899,839 | 2/1990 | Dessertine et al. ................ 364/413.02 |
| 4,911,327 | 3/1990 | Shepherd et al. ........................... 221/3 |
| 4,926,572 | 5/1990 | Holmes ..................................... 368/10 |
| 4,939,705 | 7/1990 | Hamilton et al. ......................... 368/10 |
| 4,941,201 | 7/1990 | Davis .................................... 340/870.31 |
| 4,942,544 | 7/1990 | McIntosh et al. ................ 364/413.02 |
| 4,970,669 | 11/1990 | McIntosh et al. ....................... 364/569 |
| 4,971,221 | 11/1990 | Urquhart et al. ........................... 221/2 |
| 4,975,842 | 12/1990 | Darrow et al. ..................... 364/413.02 |
| 5,014,798 | 5/1991 | Glynn .................................. 364/413.02 |
| 5,016,172 | 5/1991 | Dessertine ......................... 364/413.02 |
| 5,042,685 | 8/1991 | Moulding, Jr. et al. . |
| 5,084,828 | 1/1992 | Kaufman et al. ....................... 364/479 |
| 5,126,957 | 6/1992 | Kaufman et al. ....................... 364/479 |
| 5,170,380 | 12/1992 | Howard et al. ........................... 368/10 |
| 5,239,491 | 8/1993 | Mucciacciaro ......................... 364/569 |
| 5,345,231 | 9/1994 | Koo et al. ........................... 340/870.31 |

FOREIGN PATENT DOCUMENTS

| | | |
|---|---|---|
| 1251564 | 3/1989 | Canada . |
| 2611671 | 9/1988 | France . |
| 2648932 | 12/1990 | France . |
| 4003686 | 8/1990 | Germany . |
| 3931057 | 3/1991 | Germany . |
| 2233795 | 1/1991 | United Kingdom . |
| WO 89/09042 | 10/1989 | WIPO . |

*Primary Examiner*—Michael Horabik
*Assistant Examiner*—Timothy Edwards, Jr.
*Attorney, Agent, or Firm*—Burns, Doane, Swecker & Mathis

[57] ABSTRACT

Digital data are communicated between a portable data-gathering unit and a data-receiving unit without direct electrical connection by transmitting the data over a contactless connection system. In a preferred embodiment, data flow is bidirectional.

15 Claims, 7 Drawing Sheets

CONTACTLESS COMMUNICATION SYSTEM

This application is a continuation of Ser. No. 07/953,691, filed Sep. 28, 1992, now abandon, which is a continuation-in-part of Ser. No. 07/944,462, filed Sep. 14, 1992, now abandon, but, incorporated by reference.

BACKGROUND OF THE INVENTION

1. Field of the Invention

This invention concerns a contactless connection system and method for communicating digital information between a portable data-gathering device and a data-using device. In a preferred embodiment, it employs the system and method to communicate from a data-gathering medication event monitor to a reader-display computer/terminal. The medication event monitor is used to gather data regarding a patient's compliance with a medication regimen and/or patient-initiated or entered data concerning the patient's condition or compliance, and these data are transferred to a device where they can be read or displayed or otherwise used. Contactless connection can also be used to power up the portable device or to send other signals between the devices.

2. Background Information

There is an increasing understanding throughout the health care community that information concerning patient compliance with medication regimens is important. Understanding whether or not medications have been timely taken facilitates correct diagnosis of disease states. It also facilitates a correct understanding of drug effectiveness.

A number of devices have been proposed to keep track of a patient's drug dose taking patterns. See, for example:

U.S. Pat. No. 4,725,997, issued Feb. 16, 1988 to John Urquhart et al.;

U.S. Pat. No. 4,695,954, issued Sep. 22, 1987 to Robert J. Rose et al.;

U.S. Pat. No. 4,674,652, issued Jun. 23, 1987 to Edward M. Aten et al.;

U.S. Pat. No. 4,662,537, issued May 5, 1987 to James L. Wolf et al.; and

U.S. Pat. No. 4,616,316, issued Oct. 7, 1986 to John A. Hanpeter et al., for representative disclosures of devices which collect drug dispensing information.

In these representative devices of the art, it is common to have a clock generating a real time or elapsed time signal, a switch of some sort to signal when a dose is taken, and a memory for electronically recording the time at which each dosing signal is received. In these devices, this mechanism can often be associated with the container for the medication itself. This offers advantages of portability and ease of patient use.

The fact that the record of drug dose compliance is stored in the memory of a patient-portable device means that there must be a way to debrief the device and download the device memory. This makes the information contained in the memory accessible to the health care professional overseeing the patient's progress or to the patient him- or herself. This need for access means that there must be a data port of some sort provided in the medication monitor. This data port is used to access information contained in the memory of the patient-portable device and also can be used to feed information into the device. Examples of information which might be fed into the device include a desired dose regimen. The patient-portable device could use this information to trigger alarms at suitable time intervals. The information could also be general instructions or the like for the device to display to the patient at dosing times. An explanation of these types of displays is provided in above-referenced U.S. Pat. No. 4,725,997, which is incorporated herein by reference.

Heretofore, this data port in the medication event monitoring unit has been in the form of a multi-terminal plug body. In the field, however, a plug body connection can have shortcomings. For one, the plug body can short out if wet, which can occur in bathroom and kitchen settings. For another, it can become clogged with debris, especially with pill containers which are often carried in pockets or purses. In addition, since these devices are typically quite small and the plug bodies miniaturized, there is a real opportunity for misuse and damage during the connecting and disconnecting with the plug body. A need has been identified for a device and method for quickly and accurately providing a data transmission port into and out of portable data-gathering devices. This need arises in many applications. These can include transmitting digital information into and out of time clocks, into and out of digital recorders, and the like. An improved port into portable data-gathering devices might also be advantageous for feeding power into the device.

BRIEF DESCRIPTION OF THE INVENTION

The present invention relates to the use of contactless communication between a portable data-gathering device and a data-processing/using device. The contactless coupling of this system can be used to communicate data from a portable data-gathering unit to a data-processing/using device. It also can be used to transmit other information between the units and to feed power to the portable unit.

The contactless communication system most commonly employs inductive coupling between the two units but also may employ a pulsed or modulated low power radio-frequency signal, or an optical or a sonic or ultra-sonic signal to communicate data between the data-gathering unit and the data-receiving unit. In use, the two devices must be brought into operative proximity of each other to effect the coupling. In the case of inductive coupling this is a matter of a few inches or less and, in the case of other modes of communication, typically a few hundred feet or less. The data receiving unit may include the data-receiving section as an integral part or it may be coupled to a separate data-receiving unit directly or via a network.

In a preferred embodiment, the data-coupling system employs an electromagnetic inductor in the portable data-gathering unit. This inductor converts digital data gathered and stored in the data-gathering unit into a series of electromagnetic pulses. These electromagnetic pulses are detected by a second inductor in the receiving unit and converted into a series of electrical pulses. The receiving unit then processes the electrical signals so received back into digital data which are stored or displayed or otherwise employed.

In a preferred embodiment, these devices are used in the monitoring, storing and reporting of medication events with the portable data-gathering unit being a medication event monitor and the data receiving unit being a display or terminal such as for use by health care professionals interested in the patient's medication regimen compliance.

In an alternative embodiment, the data-receiving unit is equipped to send signals to the data-gathering unit over the same contactless (e.g. inductor/inductor) link. These signals communicated from the data-processing/using unit to the data-gathering unit may include patient data and program information. Patient data can be used by the data-gathering unit internally to issue warning signals or may be made available to the data-receiving unit at a later time. This allows the data-gathering unit to be programmed or the like so as to modify its behavior in the medication event monitoring process. Having patient data available within the data-gathering device for read-out by the data-receiving unit permits the data-gathering device to identify its patient when it is communicating with a variety of data-using devices. This makes the use of a particular data-gathering unit independent of a particular data processing/using unit.

Thus, in one aspect, this invention provides a contactless data communication system. The system includes a portable data-gathering unit and a data-receiving unit. The portable data-gathering unit includes a digital data generator and a memory for storing the digital data. The data-gathering unit is also equipped to retrieve the digital data from its memory and feed it as a series of electrical pulses to a first inductor. This inductor converts the electrical pulses into electromagnetic pulses. The data-receiving unit includes a second inductor. The two inductors are brought into operative proximity with one another by positioning the data-gathering unit in a predefined position relative to the data-receiving unit. The inductor coil of the data-receiving unit senses the electromagnetic pulses generated by the inductor of the data-gathering unit and converts the received electromagnetic pulses into a series of received electrical pulses. These received electrical impulses are then amplified and converted into digital data. The digital data so formed can be used in any manner. For example, the digital data can be stored for later review, can be displayed for immediate review, can be printed, or can be transmitted to another data-receiving using device, such as some computing means.

In another aspect, this invention provides a contactless method of data communication between a portable data-gathering unit and a data-receiving station. In this method, the data is gathered and stored as digital data in a memory in the portable data-gathering unit. At a later time, the data is called up from the memory and turned into a series of electrical pulses. This series of electrical pulses is fed to an inductor coil located in the data-gathering unit at a location most suitable for transmitting the data to a data-receiving unit. The digital data stream is converted by the inductor coil into a series of electromagnetic pulses. These electromagnetic pulses are received in an inductor coil located in the data-receiving unit at a location most suitable for receiving such electromagnetic signals. In this method, the pulses picked up by the inductor coil of the data-receiving unit are then converted into analog electrical pulses which are amplified and converted into digital pulses. These digital pulses represent digital data which can be thereafter stored or displayed or printed or the like.

In another aspect, the device and method of this invention can be made to operate bidirectionally by equipping the data-receiving unit with a circuit for feeding a series of electrical pulses to the second inductor and thereby generating a second series of electromagnetic pulses in the second inductor which can be sensed by the inductor coil of the data-gathering unit. In this case, the data-gathering unit is equipped with a suitable circuit to convert the series of electrical pulses generated by its inductor into digital data. This digital data is then used and/or stored in the data-gathering unit. This embodiment finds application when the data-gathering unit also provides some forms of information to the patient. For example, it may trigger an alarm or other alerting device to tell the patient when to take drug doses or it may trigger a display or the like to provide other information to the patient.

In still another preferred embodiment a third unit is employed to generate an alarm to the user. This third unit, the alarm unit, is equipped to communicate with the data-gathering unit or the data-receiving unit. Furthermore, this alarm unit may be combined with a pager-receiver for receiving information via a pager system.

In another aspect of the invention a contactless connection, and particularly an inductor/inductor coupling can be used as a power channel for powering-up the portable data gather unit. This configuration can lead to very advantageous easy recharging of the electrical power storage section of the data-collection device and permit this device to have a small power storage capacity.

BRIEF DESCRIPTION OF THE DRAWINGS

This invention will be further described with reference being made to the accompanying drawings in which.

DESCRIPTION OF PREFERRED EMBODIMENTS

Figure 1:
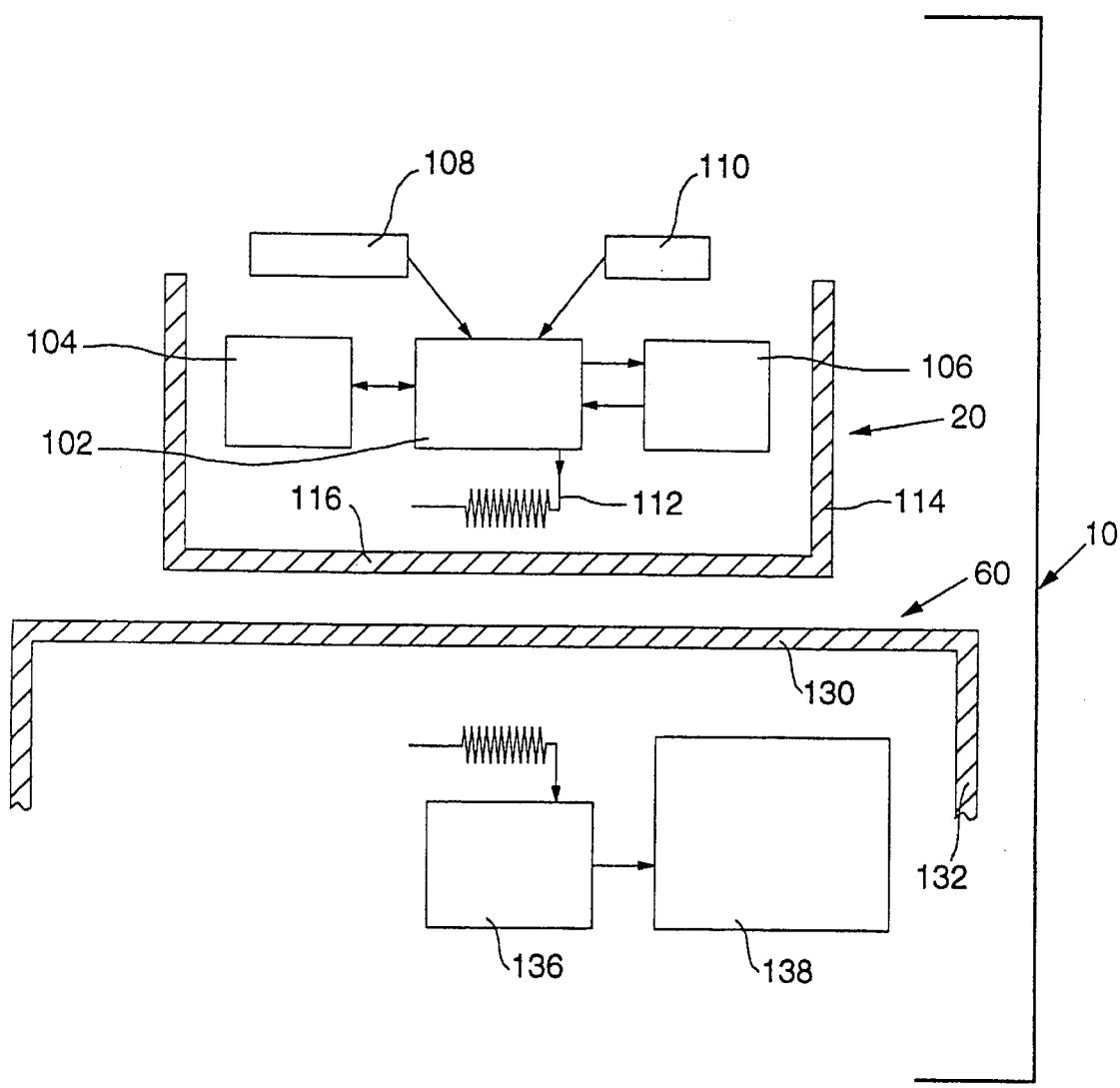
FIG. 1 is a schematic block diagram of one form of the data communications system of this invention.

FIG. 1 is an illustration of a first preferred embodiment 10 of the data communications system of the present invention. System 10 includes medication event monitoring data-gathering unit 20 and data-receiving unit 60. Data-gathering unit 20 includes a microprocessor 102 coupled to clock 104 and bidirectionally connected to memory 106 such that information can be passed into the memory 106 from microprocessor 102 and read from the memory 106 by microprocessor 102. Microprocessor 102 is also connected to event detector 108, monitors event detector 108 and performs the appropriate operations on event detection signals generated by detector 108 so that data based on these signals can be generated and stored in memory 106. The interface between event detector 108 and microprocessor 102 may be interrupt and/or inquiry based.

At least one type of medication event will cause collection of data by data-gathering unit 20. One type of event could be directly related to the medication event—for example the opening of a medicament container as an indication that a dose of medicament has been taken. In this case, event detector 108 can be a switch or the like device which can send a signal based on detecting an event. Other events which may be noted may be patient-initiated to indicate timewise compliance with some aspect of a dosing regimen. Still other events may allow monitoring the amount of medication taken by the patient or may indicate the occurrence of a certain condition for which the patient was asked to activate an event switch, that is, to manually activate a data generation signal. Any of these events can be detected by suitable means 108 with the detection signal monitored by microprocessor 102. Each time activator or event switch 108 is triggered, microprocessor 102 starts gathering digital data related to the event, for example the time that the event took place as determined by clock 104, and stores these data in memory 106.

Microprocessor 102 also is connected to event switch 110 and to inductor 112. Whenever event switch 110 detects a second type event, for example a manual switch activation or a suitable signal, it signals microprocessor 102 to change its function to reading gathered data from memory 106 and feeding the data as a stream of digital electrical pulses to inductor 112. The stream of pulses may be the digital data stream itself from memory 102 or it may be a signal suitably altered in power so as to effectively drive inductor 112. Inductor 112 converts the stream of electrical pulses into a corresponding series of electromagnetic signals.

When the data-gathering unit 20 and the data-receiving/using unit 60 are brought into operative proximity with one another, unit 60 can sense the electromagnetic signals generated by inductor 112. Inductor 112 is located close to an exterior wall 116 of housing 114. If inductor 112 is in close proximity to inductor 134 of data-receiving unit 60 the electromagnetic signals generated by inductor 112 are sensed by inductor 134, converted into a series of electrical pulses which are fed to microprocessor 136 and ultimately to data use device 138. Device 138 may be a display, a printer, a memory, a device performing data analysis operations, a data-manipulating device, a data transfer device for communicating the received data to other devices, or any other device for handling the received data. Inductor 134 is located close to wall 130 of housing 132 of data-receiving unit 60.

The system just described is a one-way system. That is, information is gathered in unit 20 and fed to unit 60 where it is displayed or otherwise used.

Figure 2:
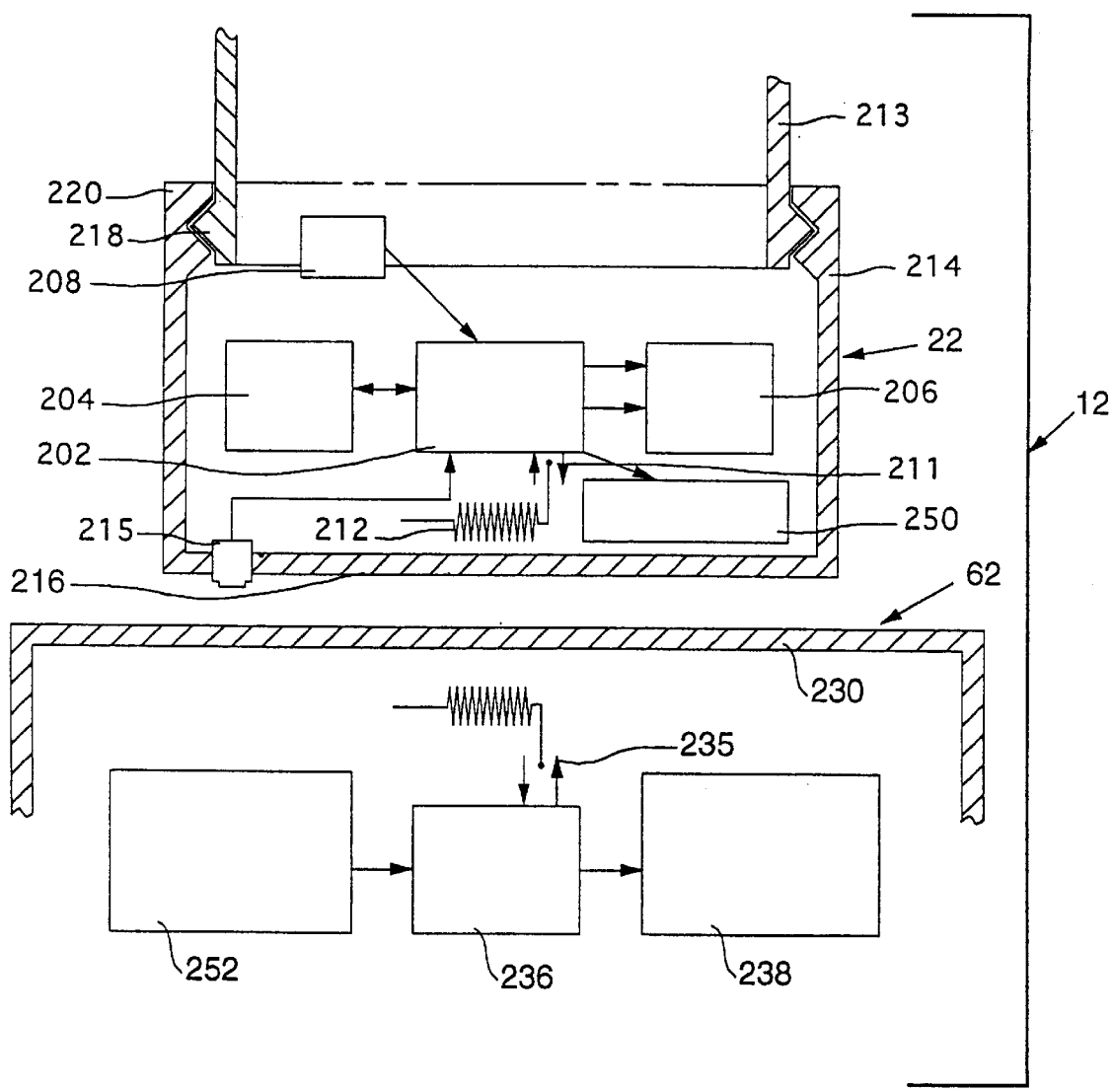
FIG. 2 is a schematic block diagram of a second, dual-direction, data communication system in accordance with the present invention in which the data-gathering device is embodied as a medication container set up to monitor a patient's compliance with a medication regimen.

In FIG. 2 a communication system 12 is shown. System 12 is a two-way system made up of data-gathering unit 22 and data-receiving unit 62. Data-gathering unit 22 is configured as a medication container 213 with cap 214. Cap 214 has a top surface comprising wall 216. Threads 218 and 220 hold cap 216 onto container 213.

In FIG. 2 container 213 is shown in inverted orientation. The data-gathering arrangement of data-gathering unit 22 includes microprocessor 202, clock 204 and memory 206. Event switch 208 is a microswitch which is located so as to be tripped whenever cap 214 is removed from container 213. A signal from switch 208 is fed to microprocessor 202 to be correlated with a time of day or elapsed time value from clock 204 and fed as digital data to memory 206. This gives a record in memory 206 of the time that a drug dose was requested by a patient by way of removing the cap of the drug container.

At preset intervals, or on demand such as by an event signal from switch 215, or on demand by a signal from data receiving unit 62, as will be disclosed below, microprocessor 202 reads data from memory 206 and passes the data through data switch 211 to inductor 212. The data which are fed to inductor 212 as a series of electrical pulses are converted into a series of electromagnetic pulses. These may be sensed by a corresponding inductor 234 in data-receiving unit 62 in housing 230, which in turn generates a series of electrical pulses. These received pulses pass through "receive/send" switch 235 into microprocessor 236 and thereafter into a data use device, i.e., printer, memory, display, a processor for analysis or calculation processes etc., 238. Switch 235 is a two state switch and connects inductor 234 into a circuit for receiving pulses from inductor 212 or for sending pulses to inductor 212. Data-gathering unit 22 contains a similar "send/receive" switch 211 for switching the function of its inductor 212.

Data-gathering unit 22 can additionally contain other function units such as, for example, display or alarm device 250 linked to microprocessor 202. Device 250 could be an alarm designed to give off alerting signals when a dose of medication should be taken. Device 250 could be a display or enunciator designed to provide information to the patient about the dosage regimen. These pieces of information to be displayed or otherwise employed could, in one embodiment, be stored over long time periods in memory 206 or any other memory in unit 22. This information could be periodically recalled from memory 206 by the action of microprocessor 202 and clock 204.

This information could also be recalled from memory 206 based on digital instructions sent to unit 22 by the two way communication channel to unit 62. It could also be variable stored information which could be altered and used following digital instructions provided by data-receiving unit 62. It also could be information based on digital signals communicated to unit 22 by unit 62. In this two-way communication link, the information or signals are fed via switch 235, inductor 234 to inductor 212 and thence to microprocessor 202 and to memory 206 of data-gathering unit 22. In this embodiment, data use unit 62 would include a data-providing device 252 such as a keyboard, a memory or other information source which would feed information to microprocessor 236, then to switch 235, which would then be in the send position and onto inductor 234 for transmission.

Instead of using a switch 215 other means can be employed to initiate processor 202 to transmit data to the data-receiving unit 62 in a bi-directional system. Such means may include some qualifying means to allow activation of processor 202 only if data-gathering unit 22 is operatively proximate to data-receiving unit 62.

In the preferred application just described this invention is employed in a medical event monitoring system. The data-gathering function would be carried out in a medication container, either in the cap as shown or elsewhere in the body of the device. In FIG. 2 data-gathering unit 22 is represented by a pill container 213 with a screw top 214. Other types of medication containers can be adapted for collecting data regarding the use of medication in a similar fashion. A container for liquid medication may include a drop counter or a medication pump which activate a switch generating a signal when and how much medication was dispensed. The data gathering unit may be an inhaler, a pill dispenser with pill ejector, a blisterpack for pills, or a unifunction device for displaying information or recording medical events such as side effects, clinical symptoms, clinical occurrences etc.

In this embodiment, when the patient receives a container of medication, the data-gathering device would be activated and would, during the dosage regimen, gather information about the patient's compliance with the desired dose regimen. At later times, such as when visiting the physician or when having the medication container refilled, the medication container would be placed in a reader such that its inductor coil 212 would be moved adjacent to the corresponding coil 234 in the data-receiving unit. A data report signal would be furnished by the data-receiving unit to the microprocessor of the data-gathering unit and the health care professional would then obtain the information collected in the memory of the data-gathering unit. Depending on the system, this could result in an erasure of the data in the memory or, alternatively, if adequate memory capacity was available, the information could remain in the memory in the container until a later removal. The information thus gathered in the data-receiving device 62 could be printed out so that compliance could be checked, it could be displayed for the same purpose, or the like. In addition, when the device is available to the health care professional, it would be possible to reprogram the data-gathering portion by using the two-way communication. In this manner, a new regimen could be inserted which could be used to control an alerting or enunciating device if present in the data-gathering unit. In addition, other instructions could be loaded into memory 206 and could later be furnished to the patient.

The application of this invention is not limited to the preferred area of medication event and compliance monitoring. In theory, any system in which digital data is gathered in one location by a portable device and later communicated to a separate data-using or processing device could benefit from the application of this invention. Such systems could include, for example, portable electronic notebooks for inspectors or "meter-readers" or security officers, or even communication between portable laptop or "notebook" computers and a fixed data-processing center.

Figure 3:
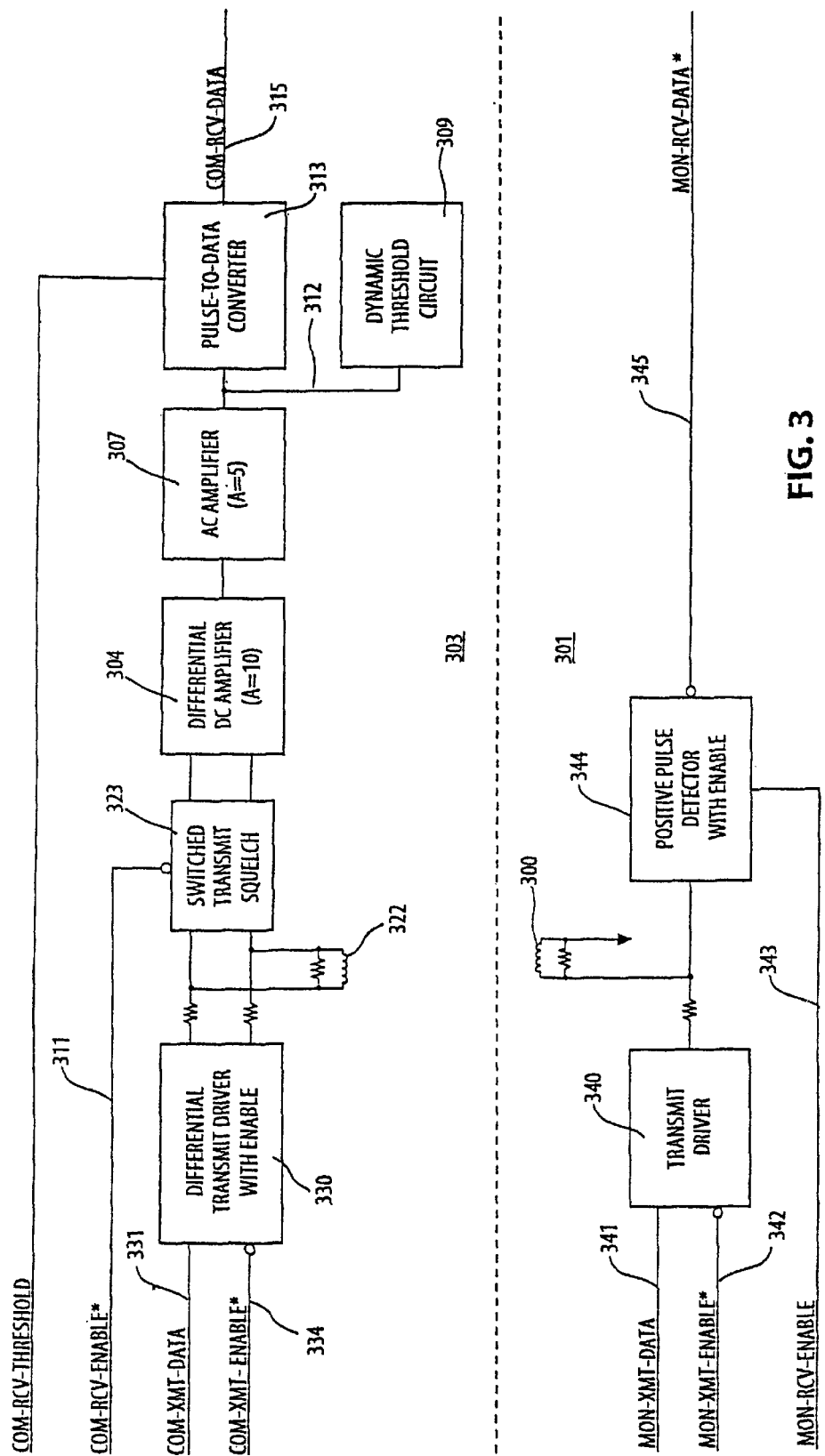
FIG. 3 is a schematic circuit diagram for an embodiment of the data-receiving unit/data-gathering unit interface of the system.

An example of suitable electrical circuitry to carry out the invention is provided in FIG. 3. FIG. 3 is a schematic block diagram of a communication interface circuit which can be used for establishing bidirectional communication between a data-gathering unit 301 and a data-receiving unit 303 of the present invention. This arrangement includes inductor coil 300 of data-gathering unit 301 and inductor coil 322 of data-receiving unit 303. When communicating data from data-gathering unit 301 to data-receiving unit 303 inductor 300 generates a electro-magnetic field which is sensed by inductor 322 at an operatively proximate distance of from about 0 to about 0.5 inches. When communicating data from data-receiving unit 303 to data-gathering unit 301 inductor 322 generates a electro-magnetic field which is sensed by inductor 300 at similar distances. To reduce power requirements in the data-gathering device 301 a dual mode of operation is employed: a communication mode and a wait and data-gathering mode. All communication operations are initiated by the data-receiving unit 303. The first transmission from 303 includes activation of the sending inductor 322 for a period of 4 command bit cells to allow the receive circuit of the data-gathering device 301 to settle. After transmitting the last packet the sending inductor 322 remains activated for 3 command bit times, which is interpreted by the monitoring device 301 as an end-of-packet signal.

The signal generated by inductor 322 of data-receiving unit 303 when sensing a change in a electro-magnetic field is fed to differential amplifier 304. The AC output signal of amplifier 304 is fed to amplifier 307. The AC component of the output signal of amplifier 307 is fed to dynamic threshold circuit 309 to provide a reference voltage 312. Reference voltage 312 fluctuates with the amplitude of the received and amplified signal and changes the sensitivity of amplifier 313 in accordance with the received signal. The output signal of amplifier 313 provides the proper binary logic level signal 315. Data signal 315 is sampled on the negative edge by the microprocessor of the data-receiving unit 303. This arrangement of amplifiers thus converts a stream of electromagnetic pulses induced into the inductor 322 into a stream of data pulses.

When transmitting information from data-gathering unit 301 to data-receiving unit 303, inductor 300 is driven with current pulses controlled by the microprocessor of data gathering unit 301. In the receiver circuit of the data-receiving unit 303 signal COM-RCV-Enable* on line 311 connects inductor coil 322 via switched transmit squelch circuit 323 to receive amplifier 304. Transmit squelch circuit 323 disconnects the inputs of amplifier 304 from inductor 322 and shorts the differential input of amplifier 304 if data-receiving unit 303 is not in receive mode. When transmitting information from the data-receiving unit 303 to data-gathering unit, inductor 322 is driven by data signals supplied by driver 330, which is enabled by a signal COM-XMT-ENABLE* on line 334 supplied by the microprocessor of data-receiving unit 303. Data signals to be transmitted are supplied by the microprocessor of data-receiving unit 303 via line 331.

Inductor 300 of data-gathering unit 301 is driven by a data signal received from transmit driver 340, controlled by input data on line 341 and enabling signal 342. When in receiving mode signal MON-RCV-ENABLE on line 343 enables amplifier 344 which provides a received data signal on line 345 for the microprocessor of data-gathering unit 301.

The circuits shown in FIG. 3 serve to transmit data between two devices without physical contact. The two inductors 300 and 322 are just brought into operative proximity with one another. It is understood, that certain components of the circuit of FIG. 3 can be omitted if no bidirectional transmission is required.

In the preferred embodiment of the present invention the inductor is implemented as a coreless wire coil. The diameter of the coil determines how precisely the sending and receiving inductors have to be aligned with each other for proper transmission. Instead of using wire coils the inductors can be implemented in trace form on rigid or flexible printed circuit boards.

As previously mentioned, instead of inductively generating electro-magnetic pulses or signals directly from the data signals, the data signals can be used to switch or modulate a carrier signal, and the switched or modulated carrier signal is supplied to the inductors. The receiving circuit requires a demodulator suitable for the selected modulation scheme and frequency.

The invention has been primarily described with reference to inductive coupling as the mode of contactless connection. Although inductive coupling is presently preferred, other contactless connection modes may be used, as well. A low power HF radio transmission system can be used in which the inductor coils described above are replaced by antennas of suitable size for the selected frequency range. A capacitively coupled data transmission system may be used as well. For operation in an electrically noisy environment or for other reasons the inductors can be replaced with transmission interfaces using sonic or ultra-sonic acoustic transmitters and receivers, or optical transmitters and receivers or the like. Means for converting digital data from memory into suitable sonic or optical signals are well known in the art. The data transmitted may be coded and used directly in the transmission system, or the coded data signals may be used to pulse or modulate a carrier signal.

Figure 4:
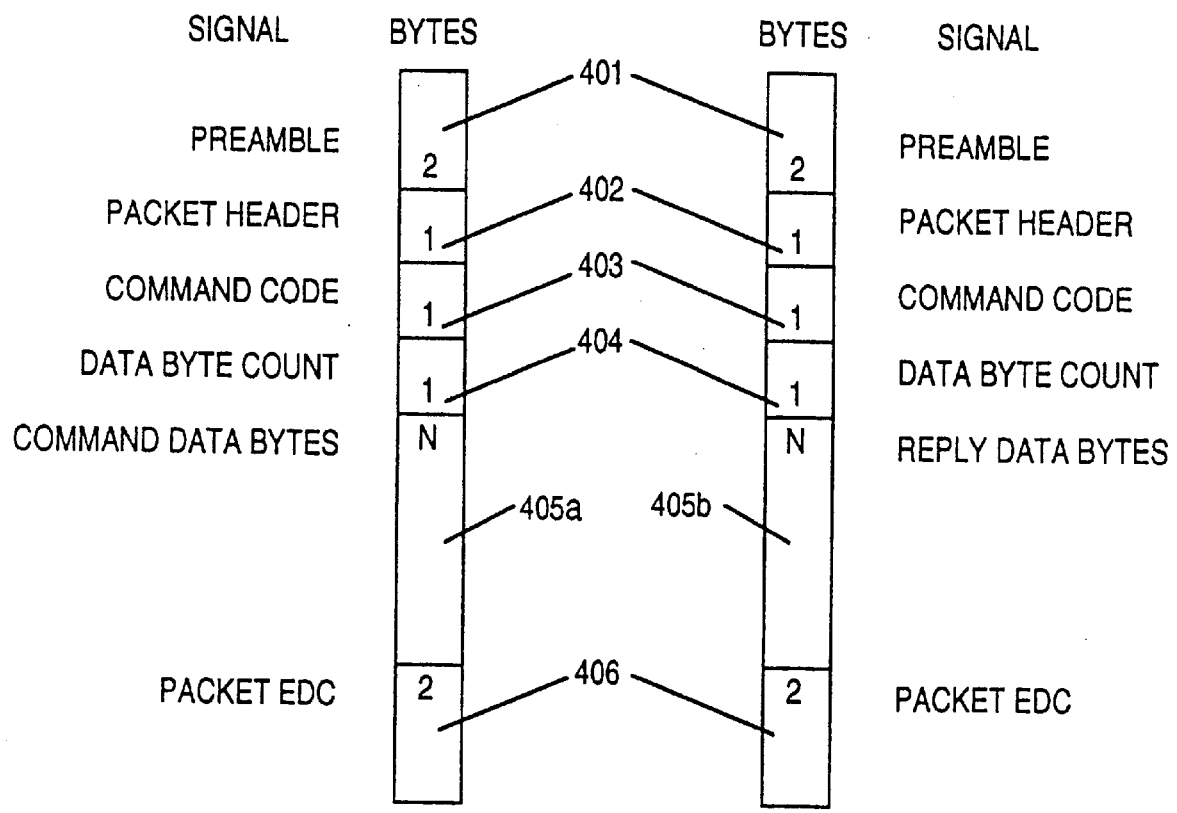
FIG. 4 is an illustration of the two types of information packets used in the communication system.

In this contactless data transmission system any suitable protocol for data communication can be used. One protocol which has proven effective utilizes packets of pulse width modulation bits organized into fields as shown in FIG. 4.

A packet consists of 2 byte long preamble field 401 made up of 16 zero bits to establish bit framing and data polarity.

This is followed by a 1 byte packet header field 402 made up of a header code and a packet sequence number.

The fourth byte carries the command code 403.

The fifth byte carries the data byte count N 404 indicating the length of the following field in bytes.

The data field 405 has a length of N bytes as indicated in the preceding byte. In a transmission to the data-gathering unit, this data field 405a may contain a request to execute a function or it may contain data to be stored in the monitoring device. In a transmission from the gathering device data field 405b contains collected data.

The last two bytes 406 carries the EDC (error detection code) which is computed from the preceding N+3 bytes.

In the communication protocol, the data-receiving unit 62 (FIG. 2) is the master device and the data-gathering unit, shown in FIG. 2 as 22, is the slave. The data-receiving unit transmits a command packet requesting that a defined function or operation be performed by the processor in the data-gathering unit. The data-gathering unit then performs that defined function and responds with a reply packet containing the result. If either packet is disrupted during transmission, the command/reply sequence is repeated until successful. The execution of a function may depend on the occurrence of another event, such as a medical event or a time event. For this reason, the contents of a command packet containing information for execution of a function at a later time is stored in local memory of the processor in the data-gathering unit.

Figure 5:
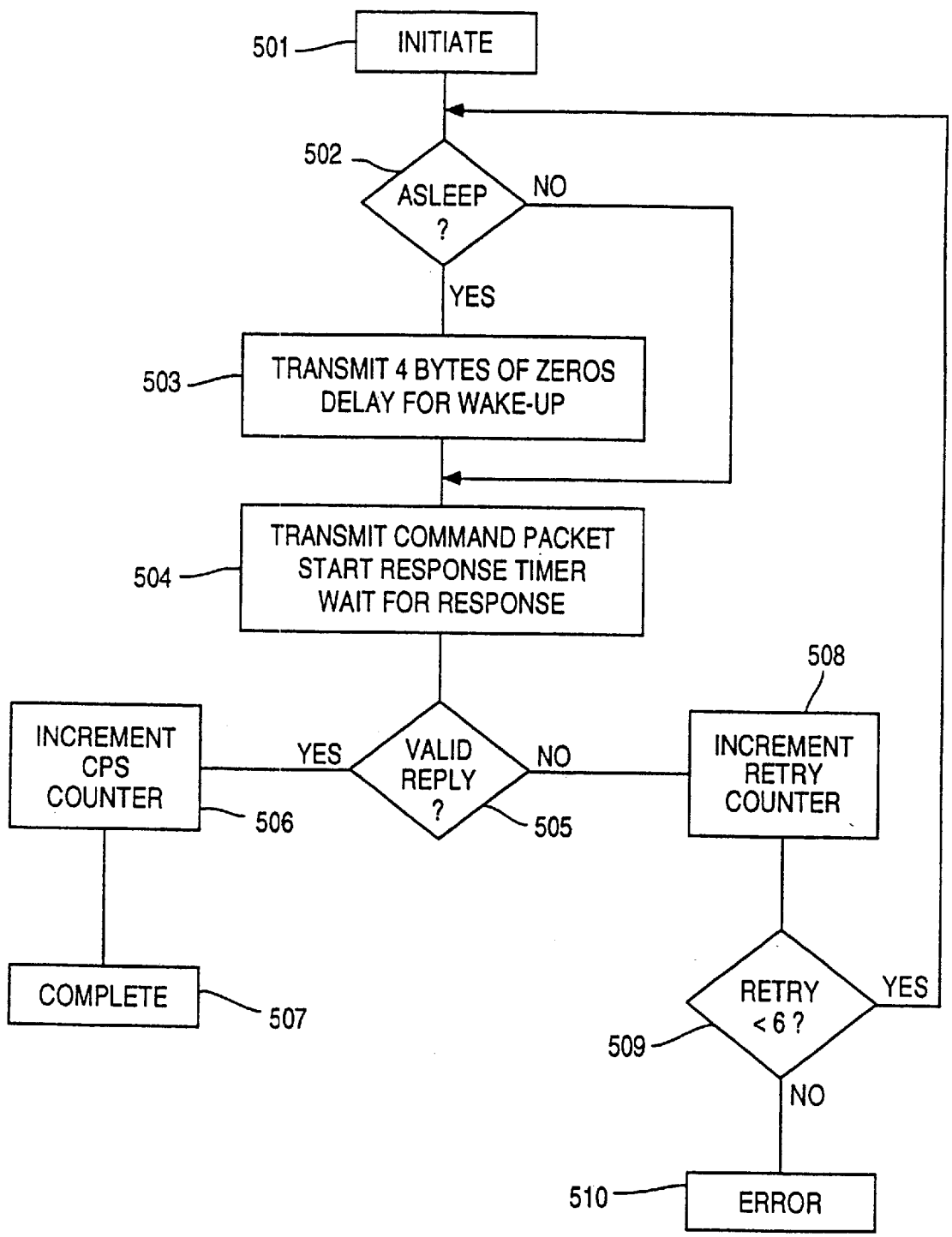
FIG. 5 is a flowchart of the data-receiving unit's transmission activities illustrating the initiation of information transfer between the data-receiving unit and the data-gathering unit.

FIG. 5 is a flowchart of the data-receiving unit's transmission activities illustrating the initiation of information transfer between the data-receiving device and the data-gathering device. This illustrates a power-saving feature that is advantageously employed. It will be recognized that the data-gathering unit can be constructed to use minimal amount of power during its data-gathering activities. Data transmission, by any of the contactless methods herein described, on the other hand requires higher rates of power consumption. Since the data-gathering device is portable any decrease in overall power usage can directly reduce the size of its batteries or other power supply. It is thus advantageous if the circuit can operate in two modes—a low power-consumption slow speed first or "sleep" mode, used during data collection, and a high power-consumption second or "awake" mode, used during data transmission.

In the protocol shown in FIG. 5, after initiation 501 of communication the data-receiving unit determines whether the data gathering unit may be in slow mode (sleep mode), step 502. The data gathering unit assumes slow speed mode about 900 msec after a transmission to the data-receiving unit. To switch a data-gathering unit into fast mode the data-receiving unit issues a predetermined number of bytes of zeroes as a wake-up call, step 503. A command packet of a structure as shown in FIG. 4 is issued in step 504.

The data-gathering unit responds to the command. If the response is evaluated as valid, step 505, the command packet sequence counter is advanced, step 506, for the next command packet transmission, and the transmission cycle is terminated, 507.

If the received response is considered invalid (step 505) the retry counter is advanced (step 508). If less than six retries have been made, the command cycle is repeated (step 509), otherwise the command cycle ends with an error flag, 510.

Figure 6:
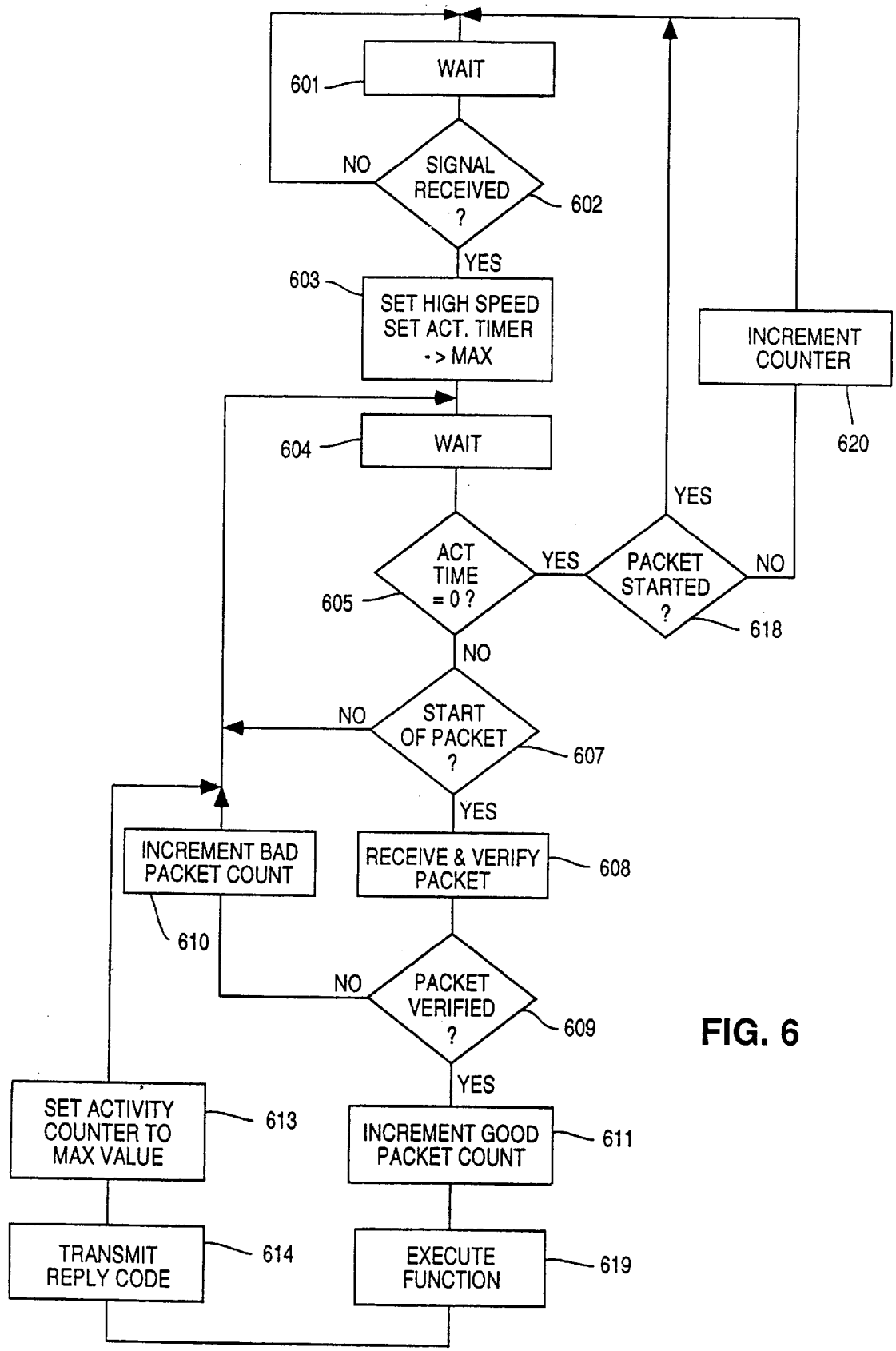
FIG. 6 is a transmission receive flowchart illustrating a data-gathering unit monitor packet transmission protocol.

FIG. 6 is a receive flowchart illustrating a data-gathering unit monitor packet transmission protocol.

The processor of the data-gathering unit idles in a low speed state 601 in which it monitors the event switches and the receive signal from the inductor coil. Events are recorded in the memory in the low speed mode. Upon recognition of received signal 602 the processor switches into high speed mode 603.

Entering high speed mode the activity counter is set to a maximum value. Then the processor waits 604 for receiving a signal. If the activity counter times out 605 and no packet start was detected 618 the processor increments the aborted communication counter 620 and returns to wait state 601. If a packet start was detected the processor returns directly to wait state 601. Upon receipt of preamble and header bytes which are indicative for Start of Packet 607 the received packet information is checked and verified, 608 and 609. Upon recognition of a packet not structurally valid the bad packet count is incremented 610 and the processor waits for the next packet in loop 604, 605 and 607.

A verified packet causes an increment of good packet count 611. The desired function is executed 619, the reply code is transmitted 614 and the activity counter is set to maximum value. Thereafter, the processor reenters the wait loop for the next packet in loop 604, 605 and 607.

Figure 7:
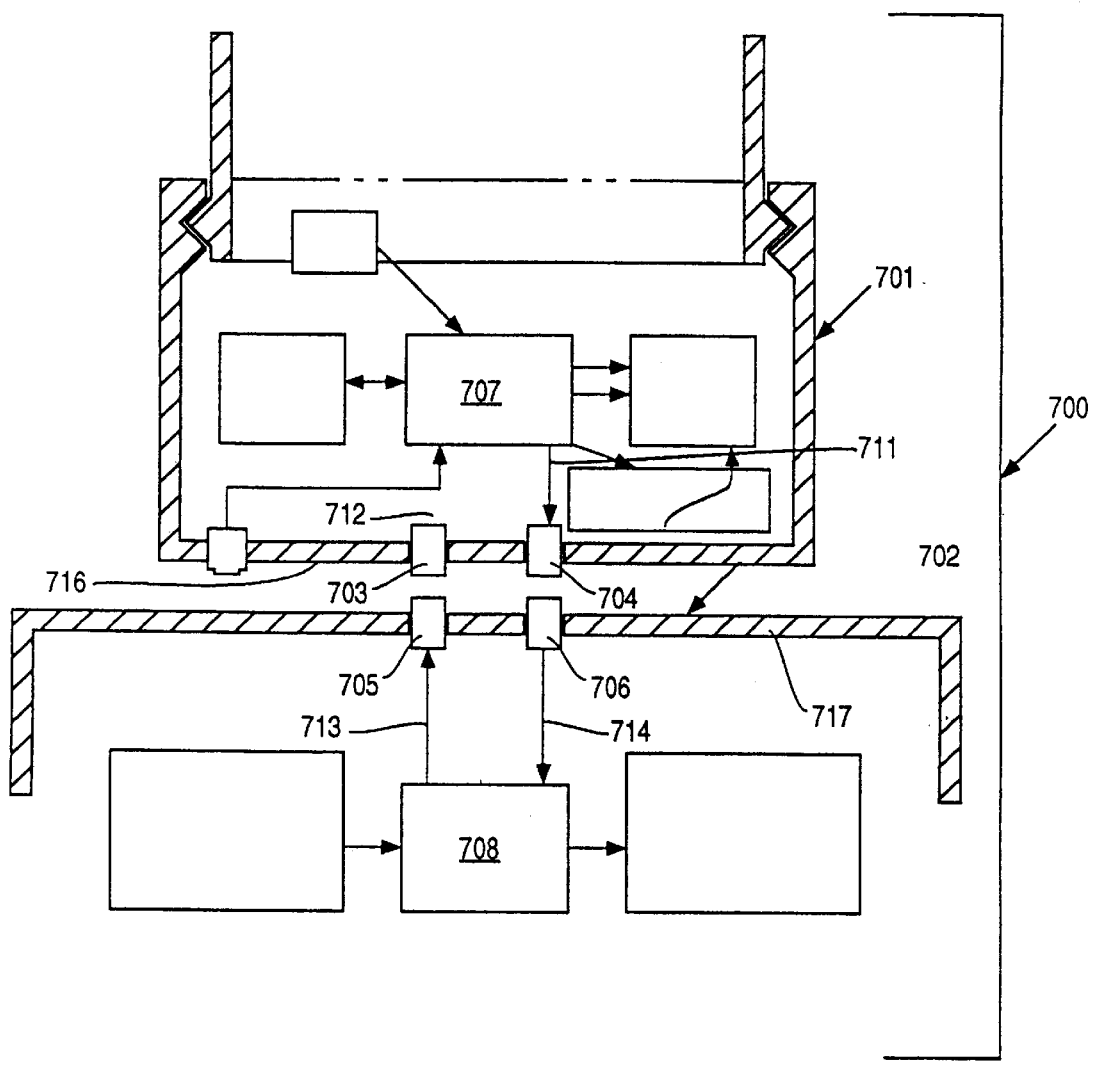
FIG. 7 is an illustration of an electro-optical interface between a data-gathering unit and a data-receiving unit.

FIG. 7 is an illustration of an electro-optical interface between data-gathering device 701 and data-receiving device 702. Processor 707 in data-gathering unit 701 corresponds to processor 202 of data-gathering unit 22 in FIG. 2. Processor 708 corresponds to processor 236 in data-receiving unit 62 in FIG. 2. The arrangement 700 in FIG. 7 corresponds to arrangement 12 in FIG. 2 except for the differences in the implementation of the contactless communication. For bidirectional communication each of the units have a light emitting device 704 and 705 such as a light emitting diode, and a photo sensor 703 and 706 such as a photo diode. The optical elements of the electro-optical interface are mounted in conforming surfaces 716 and 717 of data-gathering unit 701 and the data-receiving unit 702. Light emitting device 704 receives electrical signals via line 711 from processor 707. Photo diode 703 provides electrical signals to processor 707 via signal line 712.

In data-receiving unit 702 light emitting device 705 receives electrical signals from processor 708 via signal line 713; light sensing device 706 provides an electrical signal to processor 708 via line 714. Sense and drive amplifiers may be provided in the interface connections 711, 712, 713, and 714 between the optical driver and sensors and the associated one of processors 707 and 708.

Operation of the transfer of data between data-gathering unit 701 and data-receiving unit 702 can be performed in the same order and under the same protocol as disclosed above in reference to data transfer using electromagnetic pulses and inductors.

The communication system may be equipped with a receiver for signals of a pager system. These pager signals may contain alert signals which control the generation of optical, acoustical or other types of alert signal for the user of the data-gathering unit.

In another variation of the system of this invention the user alarming functions if present may be in a patient-notable alarm device which is separate from the data-gathering unit. In this variation, the user notes an alarm and records a medical event in response to it. The alarm can be reset by contactless communication of data between the alarming device and the data-gathering unit which would have noted the medication event or a data-using unit in a similar fashion as disclosed above for the communication between a data-gathering unit and a data-receiving unit. Furthermore, the alarming device may be triggered and reset remotely from a centralized system such as using a pager system as just described, providing a communication path directly from a health care professional to the user.

In still another variation, the data-gathering unit includes a circuit for converting energy transmitted to it via separate inductors or the same inductors used for transmitting data between the data-receiving unit and the data-gathering unit. The transmission of energy may be performed independently from any data transmission or concurrent with a data transmission between the two units. The transmitted energy may be stored in the data-gathering unit such as in a rechargeable battery or a capacitor. The transmission of energy can be performed at a frequency easy to separate from the frequency band used for transmitting data from the data-receiving unit to the data-gathering unit. The energy recovery circuit used for converting the received transmitted energy to D.C. for storage in the data-gathering unit may include a circuit for deactivation when transmitting data from the data-gathering unit to the data receiving unit.

If separate inductors are used for transmitting data and energy, the two sets of inductors can be located so as to reduce or prevent interference between energy transmission and data transmission.

The inclusion of a second power supply rechargeable by wireless energy transmission allows to separate the power consuming communication operation from the low-power data-gathering operation. The so-transmitted energy can be stored for communication operations over short time spans. An energy transmission can be performed just shortly prior to an intended data transmission. The separation of power supplies for data gathering and for communication operations allows the use of smaller batteries. In such an application, the main power supply of the data-gathering unit is used exclusively for data gathering and alerting operations.

The specific circuitry and communication protocols set forth herein are merely representative. Other systems, employing the contactless coupling of this invention could be used as well. Other systems, employing the contactless coupling of this invention could be used as well.

What is claimed is:

1. A contactless digital data communication system for use with a patient operated medication package comprising:
    a portable data-gathering unit for collecting, storing and transmitting digital data related to the occurrence of medication-taking events, wherein said portable data-gathering unit is physically integrated within the patient operated medication package; and
    a data-receiving unit comprising
        means for effecting contactless digital data communication between said data-gathering unit and said data-receiving unit;
    the data-gathering unit comprising
        a first housing having a first surface, said first surface having a first contour,
        means for collecting digital data related to the occurrence of medication-taking events and the times of said events,
        a memory for storing the collected digital data,
        means for retrieving the collected digital data from the memory and generating from the retrieved data a first electrical signal,
        a first inductor, located within said first housing adjacent to said first surface and connected to the means for retrieving, said first inductor converting the first electrical signal into a first electromagnetic signal; and
    the data-retrieving unit comprising
        a second housing having a second surface,
        said second surface having a second contour, the first and second contours being matched to permit the first and second surfaces to substantially couple when the data-gathering unit is positioned upon the data-receiving unit with the first surface in contact with the second surface,
        a second inductor located within said second housing adjacent to said second surface and positioned for sensing the first electromagnetic signal when the data-gathering unit is positioned in operative proximity upon the data-receiving unit, said second inductor converting the sensed first electromagnetic signal into a second electrical signal,
        means for converting the second electrical signal into first received digital data, and
        means for using the first received digital data so received to apprise said occurrence of medication-taking events.

2. The contactless digital data communication system of claim 1 wherein the first and second surfaces are substantially flat.

3. The contactless digital data communication system of claim 1 wherein at least one of the inductors is selected from a ferrite core inductor, a printed circuit inductor, a printed flex-circuit inductor and a core-less wire coil.

4. The contactless digital data communication system of claim 1 configured for bidirectional communication between the data-gathering unit and the data-receiving unit, the data-receiving unit further comprising
    means for feeding a third electrical signal to the second inductor for generating a second electromagnetic signal in the second inductor, said second electromagnetic signal being sensible by said first inductor when the data-gathering unit and data-receiving units are in operative proximity to one another, so that the first inductor converts said second electromagnetic signal into a fourth electrical signal;
    the data-gathering unit further comprising means for using the fourth electrical signal.

5. The bidirectional contactless digital data communication system of claim 4 wherein the data-gathering unit includes a clock for providing time information concerning the times of occurrence of medication events and wherein said collected digital data comprises this time information.

6. The bidirectional contactless digital data communication system of claim 4 wherein the data-receiving unit uses the received digital data as a record of the occurrence of medication-taking events.

7. The contactless digital data communication system of claim 4
    the data-receiving unit further comprising
        a source of digital information and
        means for generating from said digital information the third electrical signal, and
    in the data-gathering unit the means for using the fourth electrical signal further comprising
        means for converting the fourth electrical signal into received digital information and means for using the received digital information.

8. The contactless digital data communication system of claim 7 wherein the means for using the received digital information comprises means for storing the received digital information.

9. The contactless digital data communication system of claim 7 wherein the data-gathering unit further comprises means for processing the collected digital data and means for controlling the means for processing with said received digital information.

10. A bidirectional contactless medication event monitoring system comprising:

a portable medication event data-gathering unit physically integrated into a lid portion of a patient operated medicine container, said medicine container being constructed to hold medication consisting of pills, capsules or tablets, and a data-receiving unit, wherein data relating to medication taking events is communicated between said portable medication event data-gathering unit in the lid portion of the medication container and said data-receiving unit, the portable medication event data-gathering unit comprising means for collecting digital data concerning the occurrence of medication-taking events, a memory for storing the collected digital data, means for retrieving the collected digital data from the memory, means for generating from the retrieved data a first electrical signal, and means for converting said first electrical signal into a first contactlessly-communicatable signal;

the data-receiving unit comprising means for receiving said first contactlessly-communicatable signal, means for converting the received first contactlessly-communicatable signal into a second electrical signal, means for converting the second electrical signal into first received digital data, and means for using the first received digital data to apprise the occurrence of said mediation-taking events;

the data-receiving unit further comprising a source of digital information, means for generating from said digital information a third electrical signal, and means for converting said third electrical signal into a second contactlessly-communicatable signal; and the data-receiving unit further comprising means for receiving said second contactlessly-communicatable signal, means for converting the received second contactlessly-communicatable signal into a fourth electrical signal, means for converting the fourth electrical signal into received digital information, and means for using the received digital information.

11. The bidirectional contactless medication event monitoring system of claim 10, wherein the data-receiving unit additionally comprises a power transmitting coil, and means for generating a data-gathering unit-powering amount of power in said power transmitting coil; and wherein the data-gathering unit additionally comprises a first power supply for powering the means for collecting digital data, and a second power supply for powering the means for generating the first electrical signal, said second power supply itself comprising a power receiving coil for receiving the data-gathering unit-powering amount of power from the power transmission coil when the data-gathering unit is in operative proximity to the data-receiving unit.

12. The bidirectional contactless medication event monitoring system of claim 10, wherein the data-gathering unit comprises means for operating in a power conservation, data gathering mode and an active communications mode.

13. The bidirectional contactless medication event monitoring system of claim 12, wherein the data-gathering unit further includes means for monitoring the fourth electric signal, means for noting the occurrence of a stream of signals therein, and means for switching the data-gathering unit from its power conservation, data gathering mode of operation to its active communications mode of operation when said stream of signals is noted.

14. The bidirectional contactless medication event monitoring system of claim 12, wherein the data-gathering unit includes timing means for switching the data-gathering unit from its power conservation, data-gathering mode of operation to its active communications mode of operation.

15. A method for contactless data communications between a medication event monitoring unit, housed within a patient operated medicine container, and a data-receiving unit, said medication event monitoring unit capable of generating and storing digital data related to the times at which medication events take place, and said data-receiving unit capable of recording the digital data collected by the medication event monitoring unit, the medication event monitoring unit comprising:

a first housing having a first surface, said first surface having a first contour, means for collecting digital data related to the occurrence of medication-taking events and the times of said events, a memory for storing the collected digital data, means for retrieving the collected digital data from the memory and generating from the retrieved data a first electrical signal, a first inductor, located within said first housing adjacent to said first surface and connected to the means for retrieving, said first inductor converting the first electrical signal into a first electromagnetic signal, and the data-receiving unit comprising a second housing having a second surface, said second surface having a second contour, the first and second contours being matched to permit the first and second surfaces to substantially couple when the data-gathering unit is positioned upon the data-receiving unit with the first surface in contact with the second surface, a second inductor located within said second housing adjacent to said second surface and positioned for sensing the first electromagnetic signal when the data-gathering unit is positioned in operative proximity upon the data receiving unit, said second inductor converting the sensed first electromagnetic signal into a second electrical signal, means for converting the second electrical signal into first received digital data, and means for using the first received digital data so received to apprise said occurrence of medication-taking events, said method including the steps of:

generating the digital data concerning the medication events and the time at which they occur, storing said digital data in the memory in said medication event monitoring unit, positioning a portion of said patient operated medicine container housing the medication event monitoring unit in operative proximity to the data-receiving unit, retrieving the digital data from the memory and converting it into a first electromagnetic signal with the first inductor present in the medication event monitoring unit, receiving this first electromagnetic signal with the second inductor located in the data-receiving unit, said first and second inductors positioned within their respective units are placed adjacent to one another the two inductors are in operative proximity to each other and the second inductor senses the first electromagnetic signal from the first inductor, after the second inductor senses the first electromagnetic signal, converting the first electromagnetic signal into received digital data, recording the received digital data in the data-receiving unit, generating, in the data-receiving unit, digital information to be communicated to the medication event monitoring unit located in said patient operated medicine container, converting the digital information to be communicated to the medication event monitoring unit into a second electromagnetic signal with the second inductor, sensing the second electromagnetic signal in the first inductor and converting it into received digital information, and using the received digital information in the medication event monitoring unit.

* * * * *